(12) United States Patent
Kim et al.

(10) Patent No.: US 7,355,176 B2
(45) Date of Patent: Apr. 8, 2008

(54) METHOD OF FORMING TEM SPECIMEN AND RELATED PROTECTION LAYER

(75) Inventors: Hang-Ja Kim, Hwaseong-si (KR);
Eun-Kyoung Jung, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 377 days.

(21) Appl. No.: 11/220,523

(22) Filed: Sep. 8, 2005

(65) Prior Publication Data

US 2006/0054820 A1 Mar. 16, 2006

(30) Foreign Application Priority Data

Sep. 10, 2004 (KR) ...................... 10-2004-0072456

(51) Int. Cl.
*G21K 7/00* (2006.01)
(52) U.S. Cl. ...................... 250/311; 250/307; 250/306; 250/492.21; 438/14; 438/16; 73/105; 73/801; 73/643
(58) Field of Classification Search ...................... None
See application file for complete search history.

(56) References Cited

U.S. PATENT DOCUMENTS

| 5,892,225 A | 4/1999 | Okihara |
| 6,080,991 A | 6/2000 | Tsai |
| 6,184,064 B1 | 2/2001 | Jiang et al. |
| 6,194,720 B1 | 2/2001 | Li et al. |
| 6,538,254 B1 | 3/2003 | Tomimatsu et al. |
| 2006/0097168 A1 | 5/2006 | Lee et al. |

FOREIGN PATENT DOCUMENTS

| JP | 11-183339 | 7/1999 |
| JP | 2004-042215 | 2/2004 |
| KR | 100209658 B1 | 4/1999 |
| KR | 100214551 B1 | 5/1999 |
| KR | 100253320 B1 | 1/2000 |
| KR | 1020030041602 A | 5/2003 |
| KR | 1020030043233 A | 6/2003 |
| KR | 1020030060146 A | 7/2003 |

*Primary Examiner*—Jack I. Berman
*Assistant Examiner*—Zia R. Hashmi
(74) *Attorney, Agent, or Firm*—Volentine & Whitt, PLLC

(57) ABSTRACT

A method of forming a protection layer on a specimen for TEM inspection and a method of forming a specimen for TEM inspection are provided. The method of forming a protection layer on a specimen for TEM inspection generally comprises coating a wafer slice comprising an inspection point with a protection material and compressing the protection material to the wafer slice. The method of forming a specimen for TEM inspection generally comprises cutting a wafer slice comprising an inspection point from a wafer, forming a protection layer on the wafer slice, forming a first preliminary specimen by cutting the wafer slice, forming a second preliminary specimen by grinding the first preliminary specimen, and forming a TEM specimen by etching portions of the second preliminary specimen.

19 Claims, 10 Drawing Sheets

METHOD OF FORMING TEM SPECIMEN AND RELATED PROTECTION LAYER

BACKGROUND OF THE INVENTION

1. Field of the Invention

Embodiments of the invention relate generally to a method of forming a protection layer on a TEM specimen and a related method of preparing a specimen for transmission electron microscope (TEM) inspection.

This application claims priority to Korean Patent Application No. 2004-72456 filed on Sep. 10, 2004, the subject matter of which is hereby incorporated by reference in its entirety.

2. Description of the Related Art

In general, a semiconductor device is formed by a complex sequence of processes, including one or more patterning process(es). Conventional patterning processes are adapted to form, for example, a circuit pattern on a semiconductor substrate. The patterning process may include an etching process, a diffusion process, and a metallization process. Recent trends in the use of semiconductor devices are characterized by demands for multi-functionality and high speed performance. In order to meet these demands, semiconductor devices are ever more densely integrated. Increasing integration density demands tighter tolerances on circuit patterns. In order to meet these tighter design tolerances, a greater emphasis has recently been placed on inspection and analysis (e.g., structural and/or chemical) processes and equipment implementing these processes. The transmission electron microscope (TEM) is one such piece of equipment increasingly adapted to the inspection and analysis of circuit patterns formed on semiconductor substrates. Indeed, use of the TEM is wide spread due to its high resolution and general applicability to inspection and analysis processes.

However, while the TEM provides very accurate information about an object under inspection, the inspection and analysis results provided by the TEM are heavily dependent on the quality of the exemplary specimen associated with the object. That is, TEM inspection of an entire object or structure is rarely possible under commercial fabrication circumstances, so an exemplary specimen must be prepared. Accordingly, special emphasis is laid upon a related method of preparing the specimen for TEM inspection.

Conventional TEM specimens formed to inspect a predetermined layer on a semiconductor substrate have usually been prepared using an ion milling process or a focusing ion beam (FIB) process.

In the conventional FIB process, an etching process is initiated from a neighboring point proximate the inspection point on the specimen and then moved towards the inspection point during a period in which the inspection point is being viewed as an electronic image. Using this technique, the thickness of the specimen may be easily controlled.

Examples of conventional methods used to form TEM specimens include those disclosed in U.S. Pat. No. 6,194,720 to Li et al., and U.S. Pat. No. 6,080,991 to Tsai. Li et al. disclose a method of forming a TEM specimen including first and second electron transparent segments. The first electron transparent segment is formed using a FIB technique while the second electron transparent segment is formed using a wedge forming technique. Tsai discloses a method of forming the TEM specimen comprising a thin layer taken from a portion of the object or structure being inspected.

According to yet another conventional method of preparing a TEM specimen; an inspection point—which contains a defect—is first identified (or selected) using an electronic image. Then, the semiconductor wafer is cut into a wafer slice of about 2 mm×3 mm using an ultrasonic wave cutter such that the inspection point is positioned in a middle of the specimen, thereby forming a first specimen.

The first specimen is then ground to a thickness of about 40 μm, thereby forming a second specimen. The second specimen is adhered to a nickel grid, and a protection layer is coated over the inspection point using a deposition process, thereby forming a third specimen. Both side surfaces of the third specimen are then milled by sequentially varying the current applied to a FIB process, thereby forming the TEM specimen having a vertical side surface suitable for inspection.

Figure 1:
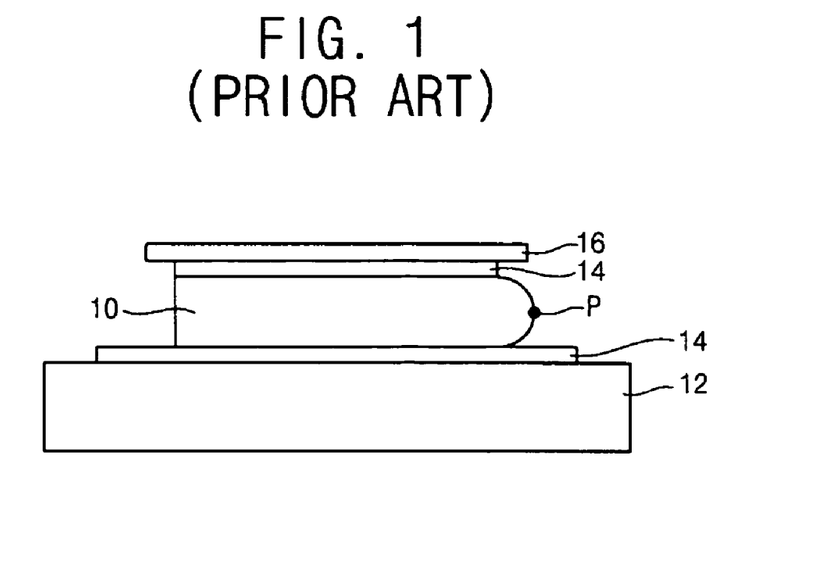
FIG. 1 is a cross sectional view illustrating a conventional method of forming a protection layer on a TEM specimen.

FIG. 1 is a cross sectional view illustrating a conventional method of forming a protection layer on a TEM specimen. More particularly, FIG. 1 illustrates one step in the foregoing conventional method adapted to the preparation of the first specimen.

Referring to FIG. 1, a first layer of protection material is deposited on a stage 12 and a wafer 10 (e.g., a preliminary specimen cut from a semiconductor substrate) is placed on the first layer of the protection material. Then, a second layer of the protection material is deposited on wafer 10. Thus, the first and second applications of the protection material form a protection layer 14 on wafer 10. A covering member 16 is then positioned on protection layer 14. Thereafter, wafer 10 is cut into a wafer slice using an ultrasonic wave cutter.

As shown in FIG. 1, although top and bottom surfaces of wafer 10 are covered by protection layer 14, the side surface(s) of wafer 10, including a beveled side surface, are barely, if at all, covered by protection layer 14. As a result, when wafer 10 is cut into a wafer slice by the ultrasonic wave cutter, the beveled side surface of wafer 10 may be broken off or otherwise removed. Accordingly, where an inspection point P is located on a beveled side surface of wafer 10, the ultrasonic wave may cause damage to inspection point P (i.e., the point of interest). When inspection point P is damaged by the ultrasonic wave, the specimen is no longer useful and a new specimen must be prepared, since TEM inspection of a broken or damaged specimen if of little value. This outcome is particularly harmful where the inspection point P is associated with a unique defect or point of interest.

Figure 2:
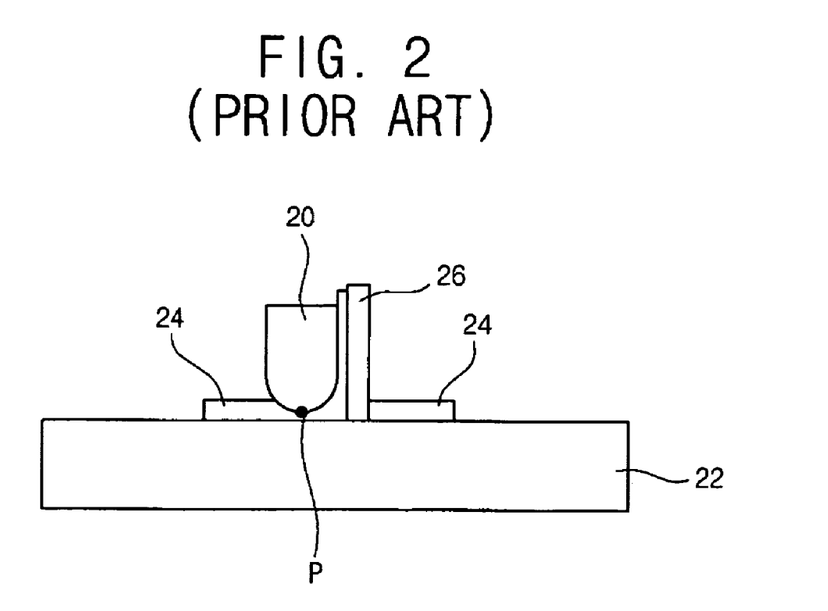
FIG. 2 is a cross sectional view illustrating one conventional method of grinding a specimen being prepared for TEM inspection.

FIG. 2 is a cross sectional view illustrating one conventional method of grinding a specimen being prepared for TEM inspection. More particularly, FIG. 2 illustrates one step in the foregoing conventional method adapted to the preparation of the second specimen.

Referring to FIG. 2, an inspection point P is again located on a beveled side surface of a first specimen 20. The beveled side surface is secured to a stage 22 using an adhesive and a covering member 26 is fixed to the vertical lateral side of the secured first specimen 20. During the grinding process, the specimen may be laterally visualized through covering member 26. Unfortunately, inspection point P cannot be viewed through covering member 26 during the grinding process, and the grinding process must be guided solely by an operator's intuition. Accordingly, the personal skill of an operator has a large effect on the grinding quality, and thus the reliability of the grinding process may be relatively low.

SUMMARY OF THE INVENTION

In one embodiment, the invention provides a method of forming a protection layer on a wafer slice to form a specimen for a transmission electron microscope (TEM) inspection, the method comprising coating the wafer slice with a protection material on top, bottom and side surfaces of the wafer slice, wherein one of the side surfaces comprises a beveled side surface comprising an inspection point, and compressing the protection material to the wafer slice.

In another embodiment, the invention provides a method of forming a specimen for a transmission electron microscope (TEM) inspection, the method comprising cutting a wafer slice from a wafer, the wafer slice comprising a beveled side surface comprising an inspection point, forming a protection layer on the wafer slice protecting the inspection point, forming a first preliminary specimen by cutting the wafer slice, wherein the first preliminary specimen comprises the inspection point, forming a second preliminary specimen by grinding top and bottom surfaces of the first preliminary specimen, wherein the second preliminary specimen comprises the inspection point, and forming a specimen by etching portions of top and bottom surfaces of the second preliminary specimen around the inspection point to respective predetermined depths.

BRIEF DESCRIPTION OF THE DRAWINGS

Exemplary embodiments will be described with reference to the accompanying drawings, in which like reference symbols indicate like or similar components. In the drawings.

DESCRIPTION OF THE EXEMPLARY EMBODIMENTS

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Figure 3:
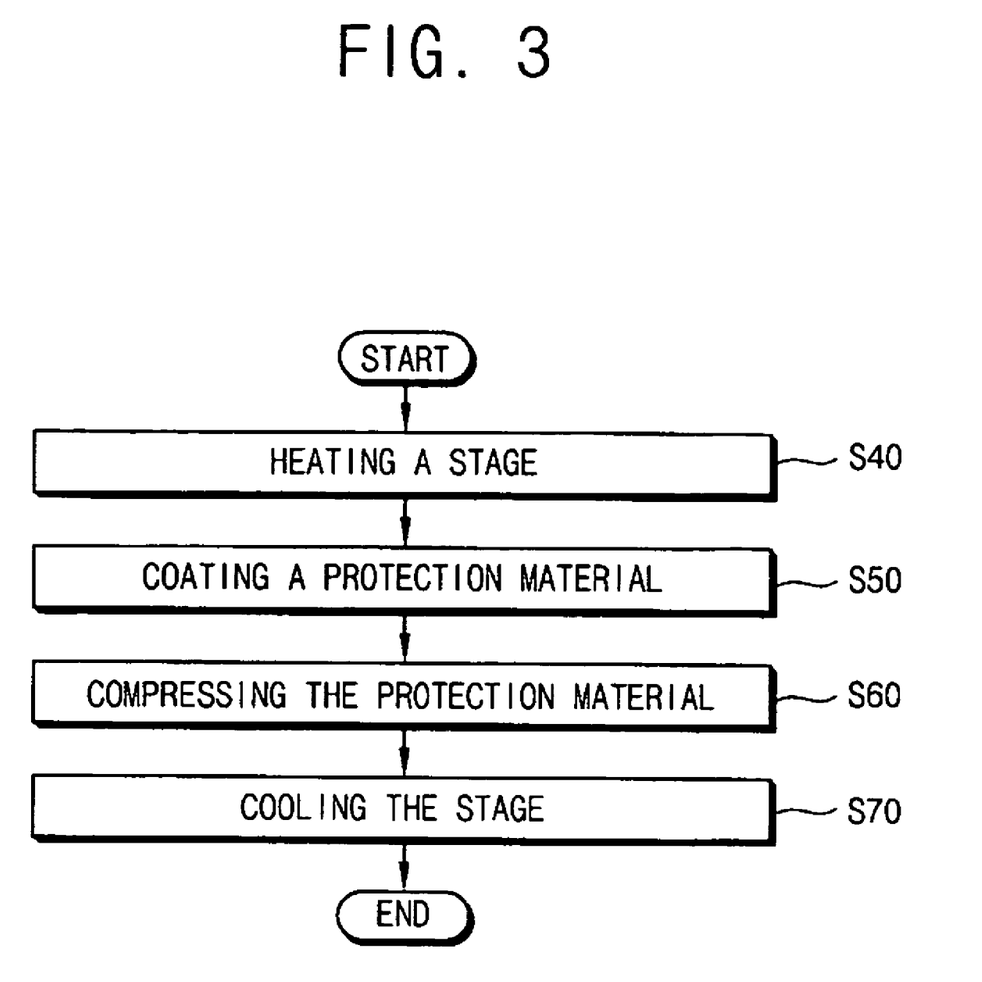
FIG. 3 is a flow chart illustrating an exemplary method of forming a protection layer for a TEM specimen.
Figure 4:
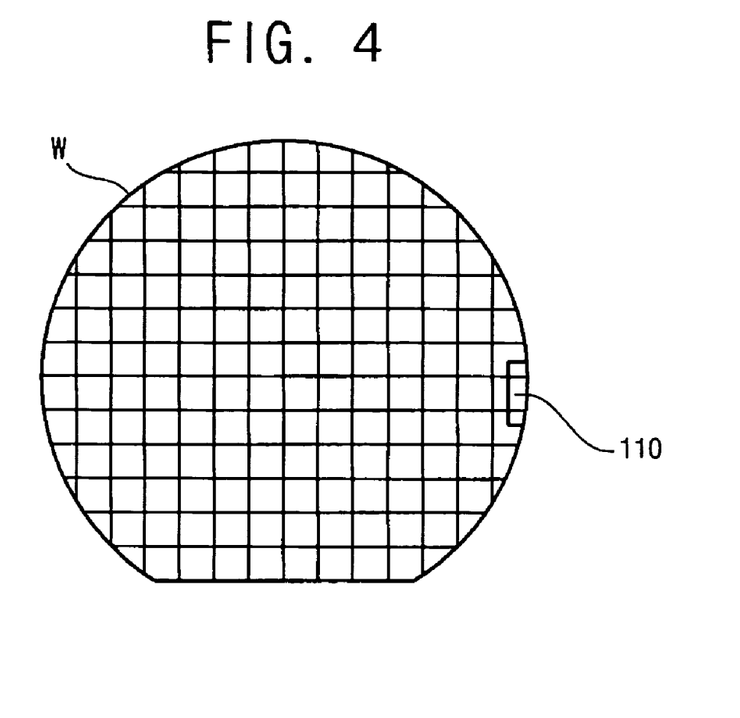
FIGS. 4 to 6 further illustrate the method of FIG. 3.
Figure 5:
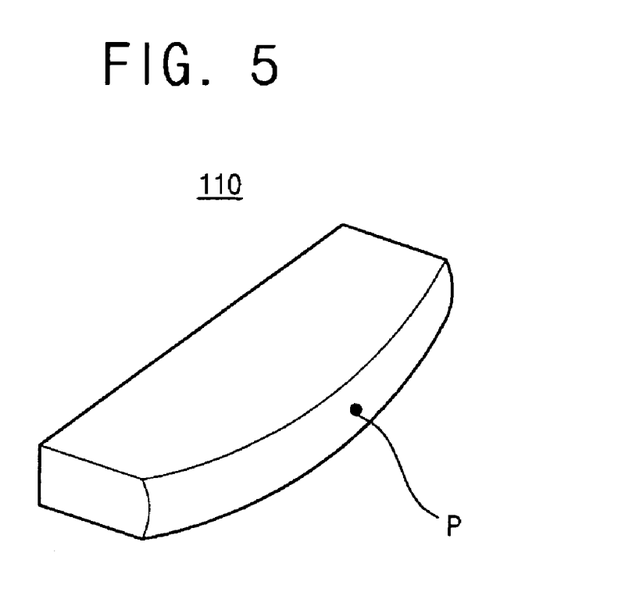
Figure 6:
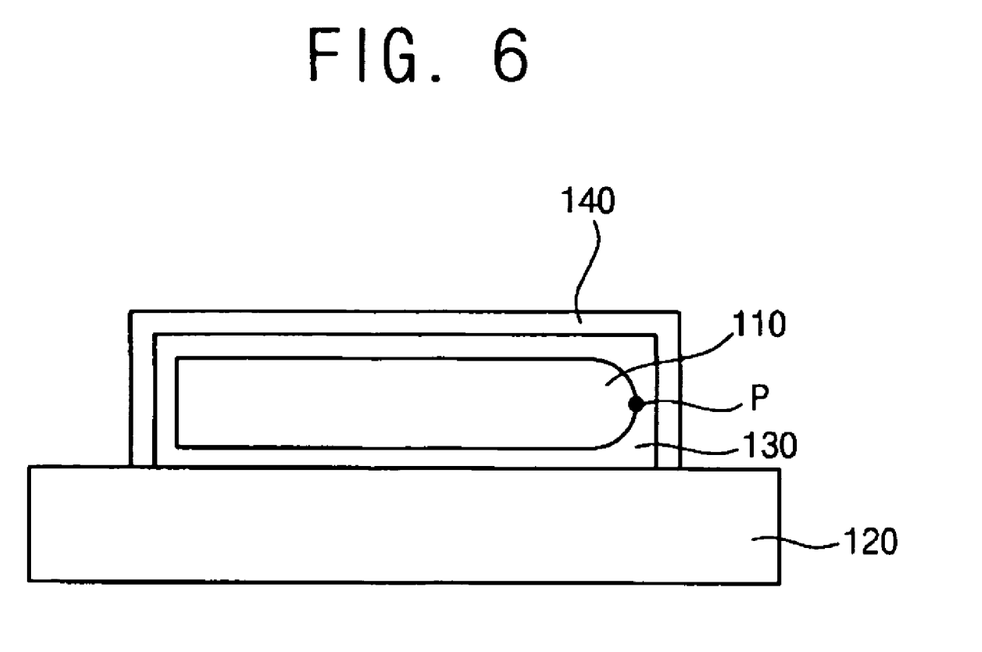

FIG. 3 is a flow chart illustrating an exemplary method of forming a protection layer on a TEM specimen. FIGS. 4 to 6 are presented to further illustrate the method of FIG. 3.

Referring to FIGS. 3 to 6, a wafer slice 110 for a TEM inspection process is provided. Wafer slice 110 will be coated with a protection layer in a subsequent process. Particularly, a wafer W is prepared for the TEM inspection process in which a layer defect or point of interest is to be inspected. The layer defect may be formed in one or more of the layers formed at a beveled side surface of wafer W. This layer defect or point of interest on the beveled side surface of wafer W will be referred to as an inspection point P. The position of inspection point P on wafer W may be determined using an electron microscope.

Once inspection point P has been located, wafer slice 110 is cut from wafer W using a diamond cutter. As shown in FIG. 5, wafer slice 110 comprises the beveled side surface surrounding inspection point P. In one embodiment, wafer slice 110 is cut to a size of about 2 cm×3 cm.

Referring to the flow chart of FIG. 3 and the illustration of FIG. 6, a stage 120 is first heated using (e.g.) a hot plate or a heater to a temperature sufficient to reflow a selected protection material (S40). In one embodiment, an epoxy resin compound is used as the protection material and the stage is heated for about 5 minutes to about 10 minutes.

Then, the top surface of stage 120 is coated with the protection material using one or more conventional processes, such as a spin coating. Wafer slice 110 is then positioned on stage 120 once it has been coated with the protection material. For example, in the illustrated example, wafer slice 110 is positioned on stage 120 lengthwise and in parallel with stage 120. Thereafter, the top surface and side surfaces of wafer slice 110, including the beveled side surface, are coated with the protection material (S50). In the illustrated embodiment, the protection material is applied such that it covers inspection point P on the beveled side surface of wafer slice 110. In a related aspect of this embodiment, the fact that wafer slice 110 is coated with the protection material only after wafer slice 110 including the beveled side surface is sufficiently heated to reflow the protection material, allows the entire surface of wafer slice 110 to be evenly coated with the protective material.

Continuing with the illustrated example, a bottom surface of wafer slice 110 is coated with the protection material when the wafer slice 110 is positioned on stage 120. Whereas, the top and side surfaces of wafer slice 110 are coated with the protection material after wafer slice 110 is positioned on stage 120.

Once wafer slice 110 is coated with the protection material, a covering member 140 is placed over it, such that wafer slice 110 is mechanically compressed (S60). In the illustrated example, the combination of the upper surface of stage 120 and covering member 140 form an enclosure of sorts for wafer slice 110 and its coating of protection material.

Covering member 140 may take any reasonable form, but will generally be shaped in accordance with the shape of wafer slice 110, such that the top and side surfaces of wafer slice 110 are enclosed within covering member 140. In one embodiment, covering member 140 takes the form of a hollow hexahedron having an opening in its bottom portion. A side portion of this exemplary covering member 140 has a curvature corresponding to that of the beveled side surface of wafer slice 110. Covering member 140 will typically be designed to fit snuggly around wafer slice 110. In one embodiment, covering member 140 is formed from glass having a thickness of about 0.1 cm.

As stage 120 is cooled to around room temperature (S70), the protection material is hardened around wafer slice 110 to form a protection layer 130 covering at least inspection point P. Protection layer 130 covers the beveled side surface of wafer slice 110, such that inspection point P is not damaged during subsequent preparation steps, such as a step in which wafer slice 110 is cut using an ultrasonic wave cutter.

In the foregoing exemplary embodiment, the protection layer is entirely formed on wafer slice 110 after the wafer slice is cut from wafer W. However, the protection layer may be, at least partially, formed on the wafer before wafer slice 110 is cut.

Figure 7:
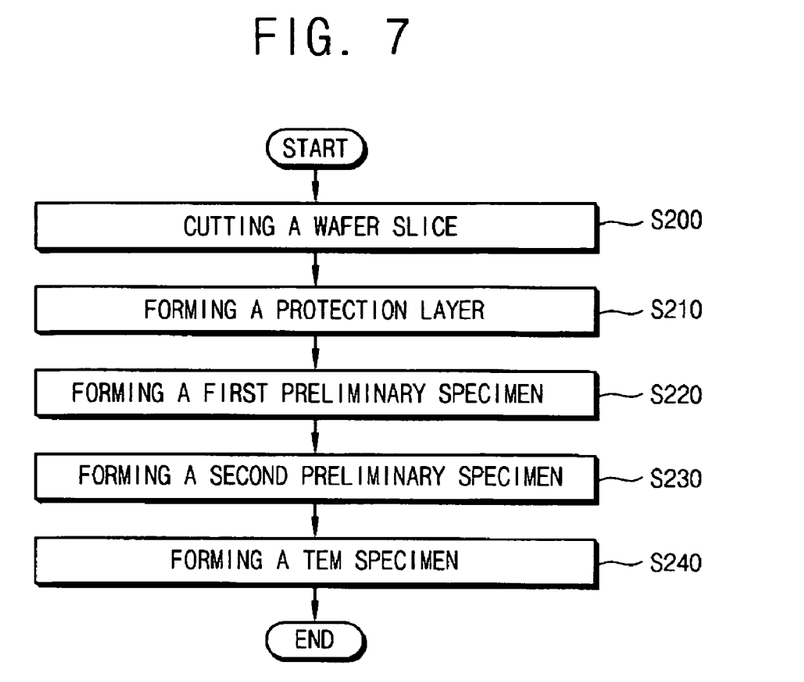
FIG. 7 is a flow chart illustrating an exemplary method of forming a TEM specimen.

FIG. 7 is a flow chart illustrating an exemplary method of forming a TEM specimen.

Figure 8:
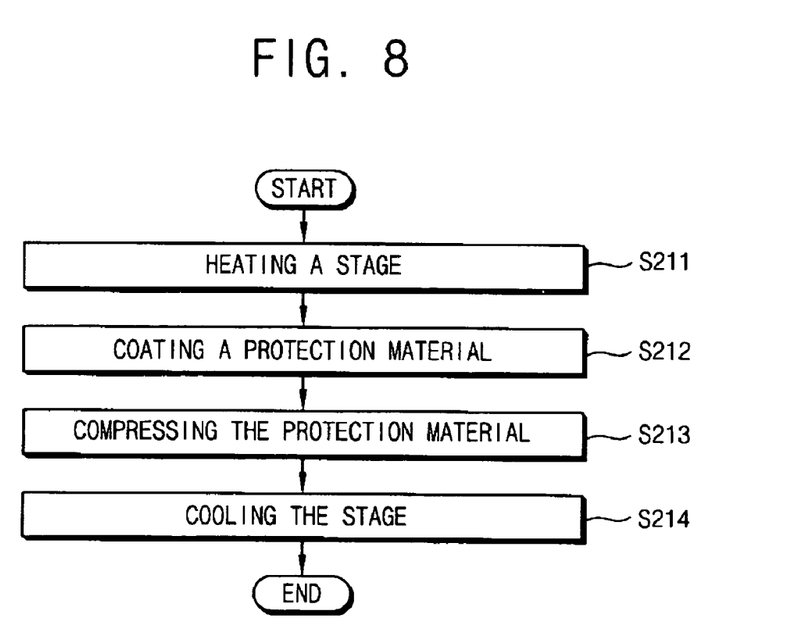
FIG. 8 is a flow chart illustrating an exemplary method of forming a protection layer on the TEM specimen.
Figure 9:
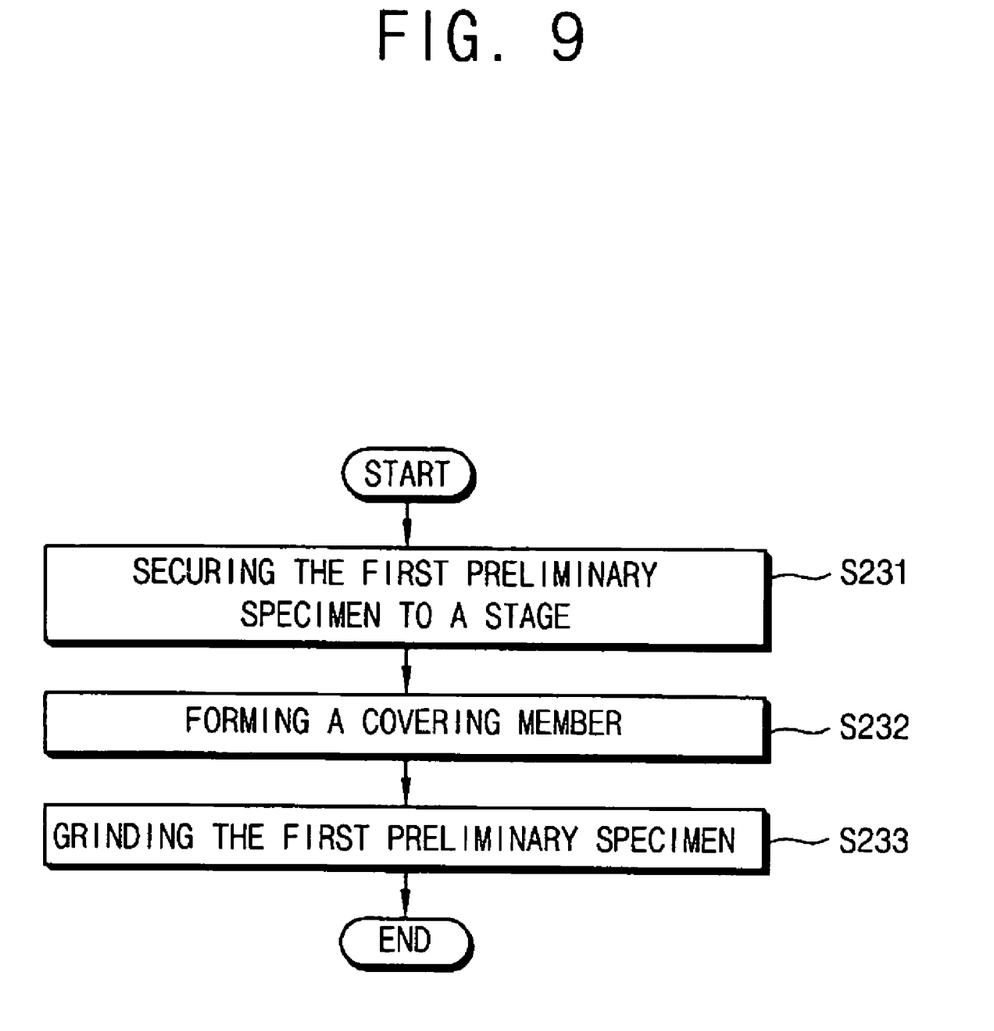
FIG. 9 is a flow chart illustrating an exemplary method of forming a second preliminary specimen by grinding a first preliminary specimen; and, FIGS. 10 to 16 further illustrate the methods of FIGS. 7-9.

FIG. 8 is a flow chart illustrating an exemplary method of forming a protection layer on the TEM specimen. FIG. 9 is a flow chart illustrating an exemplary method of forming a second preliminary specimen by grinding a first preliminary specimen.

FIGS. 10 to 16 are presented to further illustrate the methods of FIGS. 7-9.

Figure 10:
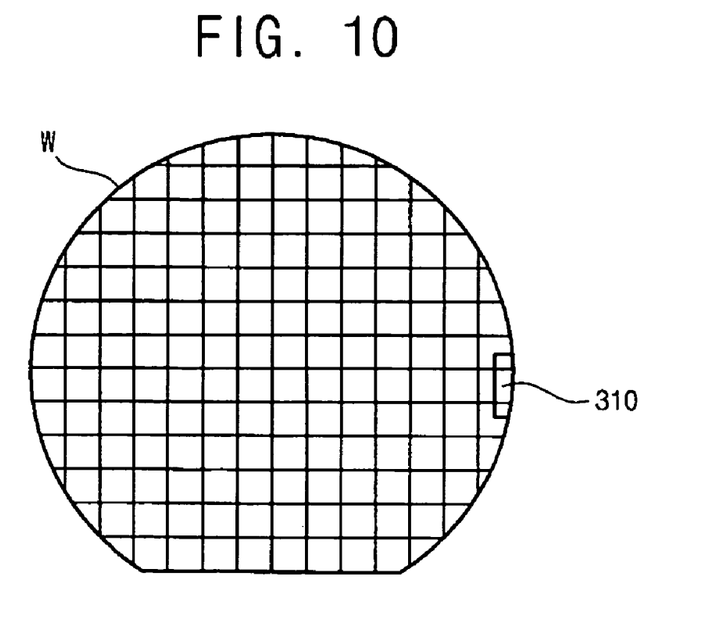

Referring to FIGS. 7 and 10, a wafer slice 310 for a TEM inspection process is provided. Wafer slice 310 will be coated with a protection layer in a subsequent process. Particularly, a wafer W is prepared for the TEM inspection process in which a layer defect or point of interest is to be inspected. The layer defect may be formed in one or more of the layers formed at a beveled side surface of wafer W. This layer defect or point of interest on the beveled side surface of wafer W will be referred to as an inspection point P. The position of inspection point P on wafer W may be determined using an electron microscope.

Figure 11:
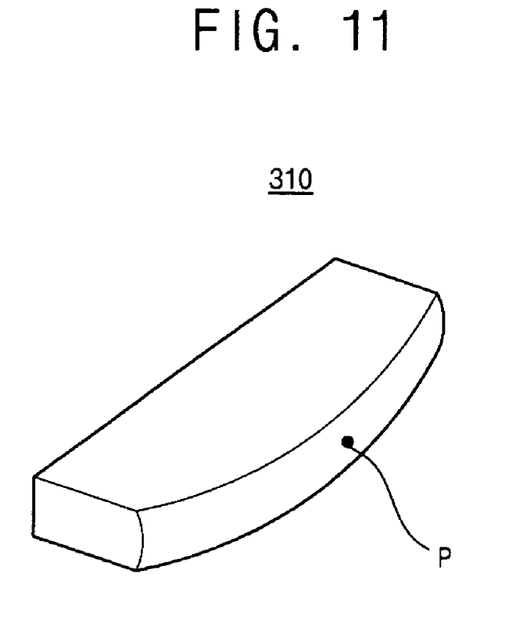

Once inspection point P has been located, wafer slice 310 is cut from wafer W using a diamond cutter. As shown in FIG. 11, wafer slice 310 comprises the beveled side surface surrounding inspection point P. In one embodiment, wafer slice 310 is cut to a size of about 2 cm×3 cm.

Referring again to FIGS. 7 and 12, a protection layer 330 is formed on wafer slice 310 (S210).

An exemplary method of forming protection layer 330 will be described in detail hereinafter with reference to FIGS. 8 and 12.

Figure 12:
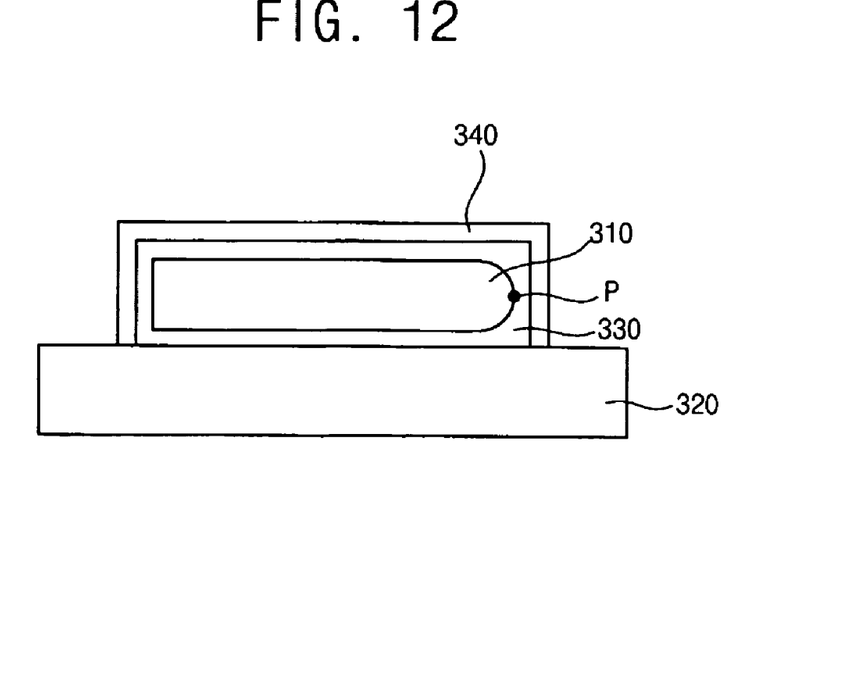

Referring to the flow chart of FIG. 8 and the illustration of FIG. 12, a stage 320 is first heated using (e.g.) a hot plate or a heater to a temperature sufficient to reflow a selected protection material (S211). In one embodiment, an epoxy resin compound is used as the protection material and the stage is heated for about 5 minutes to about 10 minutes.

Then, the top surface of stage 320 is coated with the protection material using one or more conventional processes, such as a spin coating. Wafer slice 310 is then positioned on stage 320 once it has been coated with the protection material. For example, in the illustrated example, wafer slice 310 is positioned on stage 320 lengthwise and parallel with stage 320. Thereafter, the top surface and side surfaces of wafer slice 310, including the beveled side surface, are coated with the protection material (S212). In the illustrated embodiment, the protection material is applied such that it covers inspection point P on the beveled side surface of wafer slice 310. In a related aspect of this embodiment, the fact that wafer slice 310 is coated with the protection material only after wafer slice 310 including the beveled side surface is sufficiently heated to reflow the protection material, allows the entire surface of wafer slice 310 to be evenly coated with the protective material.

Continuing with the illustrated example, a bottom surface of wafer slice 310 is coated with the protection material when wafer slice 310 is positioned on stage 320. Whereas, the top and side surfaces of wafer slice 310 are coated with the protection material after wafer slice 310 is positioned on stage 320.

Referring to FIG. 12, once wafer slice 310 is coated with the protection material, a first covering member 340 is placed over it, such that wafer slice 310 is mechanically compressed (S213). In the illustrated example, the combination of the upper surface of stage 320 and first covering member 340 form an enclosure of sorts for wafer slice 310 and its coating of protection material.

First covering member 340 may take any reasonable form, but will generally be shaped in accordance with the shape of wafer slice 310, such that the top and side surfaces of wafer slice 310 are enclosed within first covering member 340. In one embodiment, first covering member 340 takes the form of a hollow hexahedron having an opening at its bottom portion. A side portion of this exemplary first covering member 340 has a curvature corresponding to that of the beveled side surface of wafer slice 310. Covering member 340 will typically be designed to fit snuggly around wafer slice 310. In one embodiment, first covering member 340 is formed from glass having a thickness of about 0.1 cm.

As stage 320 is cooled to around room temperature (S214), the protection material is hardened around wafer slice 310 to form a protection layer 330 covering at least inspection point P.

Figure 13:
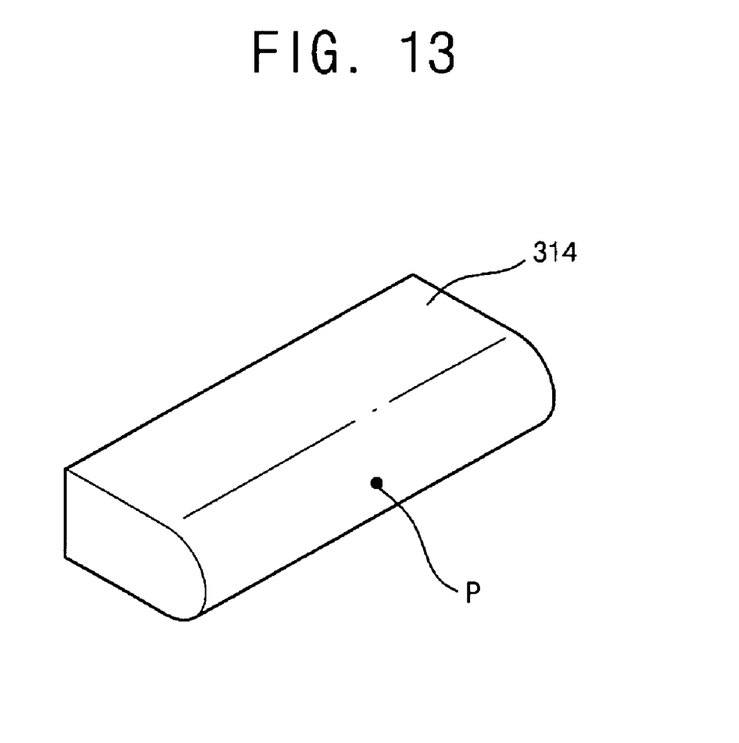

Referring to FIGS. 7 and 13, a first preliminary specimen 314 is cut from wafer slice 310 by an ultrasonic wave cutter (S220), and inspection point P is included in first preliminary specimen 314. In one embodiment, first preliminary specimen 314 is cut to a size of about 2 mm×3 mm.

Protection layer 330 covers the beveled side surface of wafer slice 310, such that inspection point P is not damaged and first preliminary specimen 314 is not broken during subsequent preparation steps, such as a step in which first preliminary specimen 314 is cut from wafer slice 310 by an ultrasonic wave cutter.

In the foregoing exemplary embodiment, the protection layer is entirely formed on wafer slice 310 after the wafer slice is cut from wafer W. However, the protection layer may be, at least partially, formed on the wafer before wafer slice 310 is cut.

Figure 14:
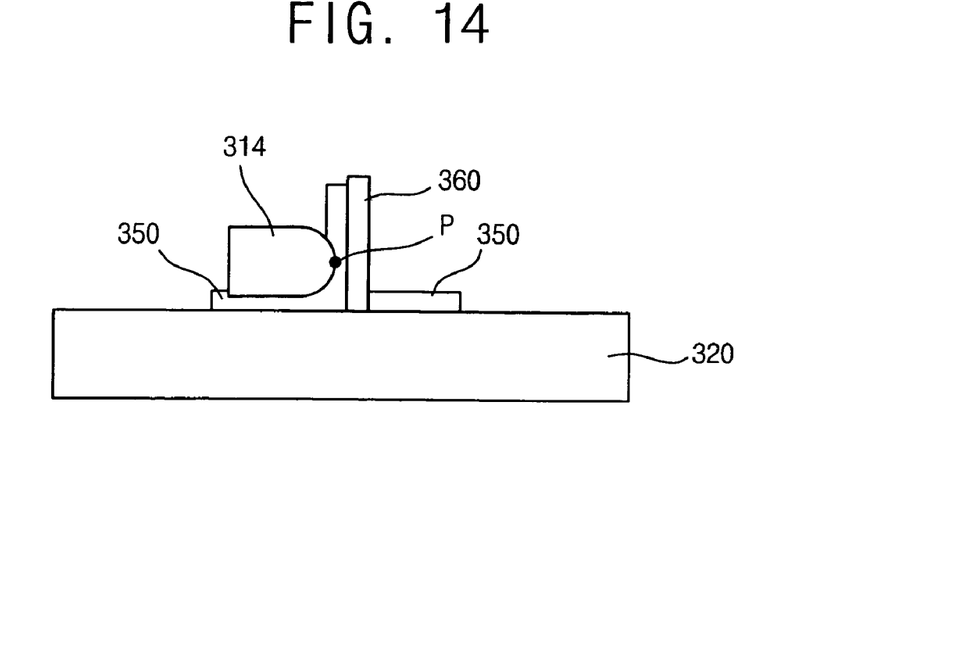
Figure 15:
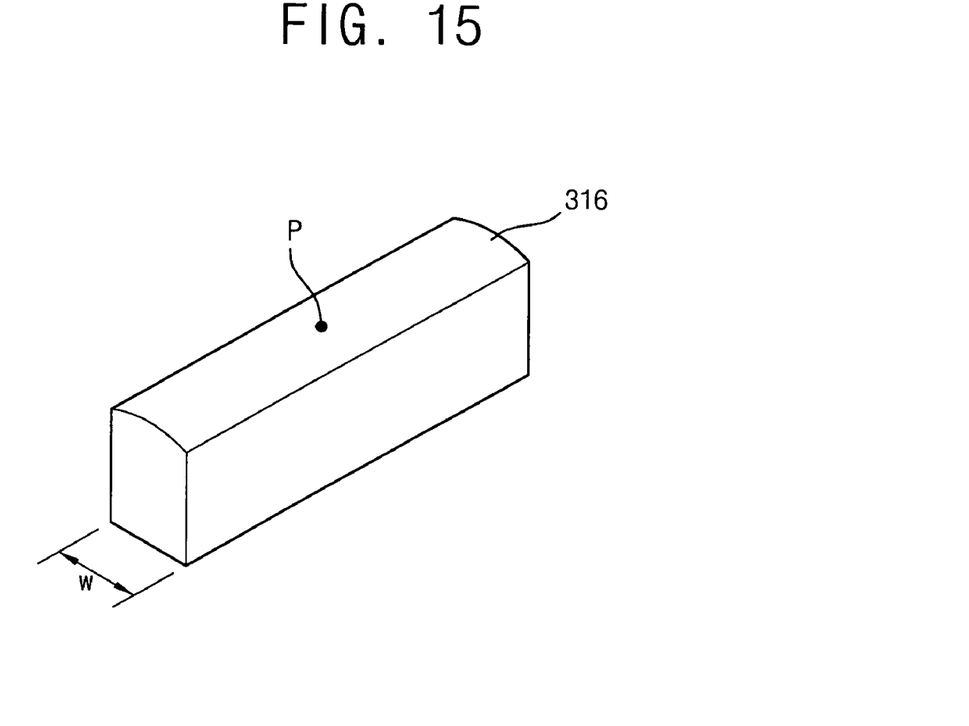

Referring to FIGS. 7 and 15, both a top surface and a bottom surface of first preliminary specimen 314 are ground to form a second preliminary specimen 316 with a predetermined thickness w (S230). The grinding process with respect to first preliminary specimen 314 will be described in detail hereinafter with reference to FIGS. 9 and 14.

Referring to FIGS. 9 and 14, first preliminary specimen 314, having a size of about 2 mm×3 mm, comprises the beveled side surface surrounding inspection point P. First preliminary specimen 314 is secured to stage 320 by an adhesive 350 in such an arrangement that inspection point P faces in a direction parallel with the surface of stage 320 (S231).

A second covering member 360 is formed at a side portion of first preliminary specimen 314 and is adapted to support first preliminary specimen 314 (S232).

In one embodiment, second covering member 360 is positioned perpendicularly with respect to stage 320, and is secured to stage 320 by adhesive 350. Second covering member 360 is also secured to first preliminary specimen 314 by adhesive 350. Second covering member 360 comprises a transparent material so that inspection point P may be viewed through an electron microscope while first preliminary specimen 314 is ground. Second covering member 360 may comprise, for example, transparent glass.

Next, top and bottom surfaces of first preliminary specimen 314 are ground simultaneously (S233), which reduces the width of first preliminary specimen 314. Since the top and bottom surfaces are symmetrical with respect to inspection point P, the width of first preliminary specimen 314 is reduced when the top and bottom surfaces of first preliminary specimen 314 are ground. In one embodiment, first preliminary specimen 314 is reduced to a width within a range of about 40 µm to about 60 µm.

Second preliminary specimen 316, shown in FIG. 15, is formed when first preliminary specimen 314 is ground while inspection point P faces in a direction parallel with the surface of stage 320. As a result, inspection point P of the beveled side surface of first preliminary specimen 314 may be viewed through an electron microscope while performing the grinding process on first preliminary specimen 314.

FIG. 15 shows a second preliminary specimen 316 created by performing a grinding process on first preliminary specimen 314.

Figure 16:
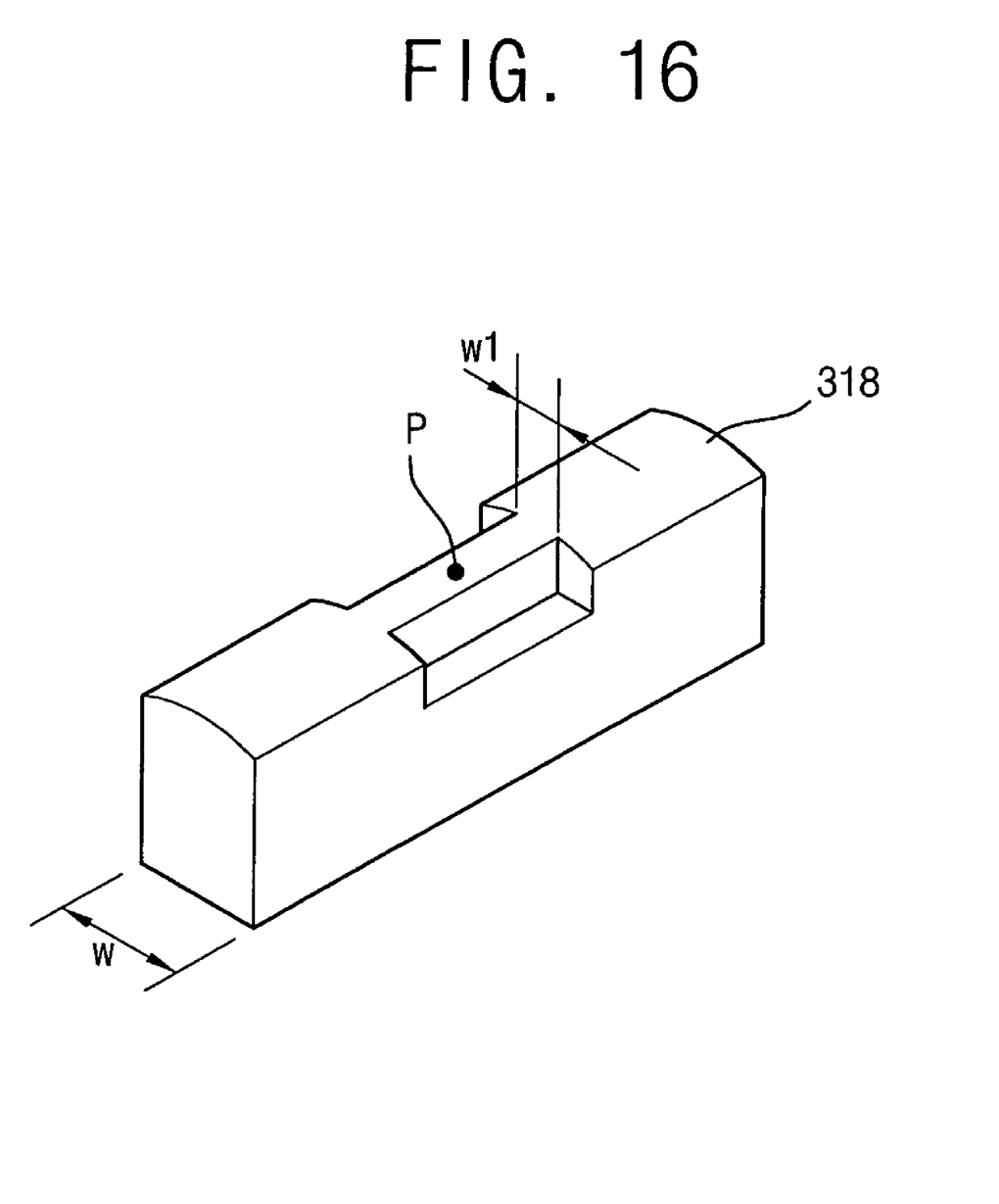

Referring to FIGS. 7 and 16, a portion of second preliminary specimen 316 around inspection point P is removed from the top and bottom surfaces thereof to respective predetermined depths by an FIB process, thereby forming a TEM specimen 318 (S240).

As shown in FIG. 16, TEM specimen 318 has recessed portions that are symmetrical with respect to inspection point P created by the FIB etching process. A reduced width w1 of TEM specimen 318 around inspection point P is much smaller than width w of an end portion of TEM specimen 318. In one embodiment TEM specimen 318 has the reduced width w1 of about 40 nm around inspection point P, so that electrons ejected from the TEM may sufficiently penetrate the TEM specimen around inspection point P. The FIB etching process may be performed by sequentially varying a current in a range from about 2700 picoamperes (pa) to about 70 pa in order to reduce the width of TEM specimen 318 around inspection point P from width w to reduced width w1. First in the FIB etching process, a coarse etching is performed at a portion of second preliminary specimen 316 neighboring inspection point P using a high current FIB process. Then, as the depth of the FIB etching portion increases, and consequently the surface of the etching portion approaches inspection point P, the current used in the FIB etching process is reduced, and as a result the FIB etching process is finer as the FIB etching portion approaches inspection point P. Accordingly, the width of second preliminary specimen 316 around inspection point P is quickly and accurately reduced to reduced width w1, thereby forming TEM specimen 318.

Also, an additional protection layer (not shown) may be formed on inspection point P of second preliminary specimen 316 prior to the FIB process to protect the TEM specimen from being damaged during either the FIB process for viewing inspection point P of TEM specimen 318 or a micro-etching process. The additional protection layer may include a tungsten (W) layer, a platinum (Pt) layer, a carbon (C) layer, an aluminum (Al) layer, etc. These can be used alone or in combinations thereof.

Thereafter, TEM specimen 318 is adhered to a grid, thereby completing the formation of the TEM specimen.

In accordance with embodiments of the present invention, a protection layer is formed on a beveled side section of a specimen on which an inspection point is formed, so that the specimen is not broken and the inspection point not damaged when the specimen is cut by an ultrasonic wave cutter. Accordingly, less time is lost during the formation of the specimen.

Furthermore, the inspection point is viewed through an electron microscope during a specimen grinding process, thereby improving the specimen quality.

Although exemplary embodiments of the present invention have been described, the present invention should not be limited to these exemplary embodiments, but rather, one of ordinary skill in the art will understand that various changes and modifications can be made while remaining within the scope of the present invention as claimed hereinafter.

What is claimed is:

1. A method of forming a protection layer on a wafer slice to form a specimen for a transmission electron microscope (TEM) inspection, the method comprising:
    coating the wafer slice with a protection material on top, bottom and side surfaces of the wafer slice, wherein one of the side surfaces comprises a beveled side surface comprising an inspection point; and,
    compressing the protection material to the wafer slice.

2. The method of claim 1, further comprising:
    heating a stage adapted to support the wafer slice prior to coating the wafer slice with the protection material; and,
    positioning the wafer slice on an upper surface of the stage.

3. The method of claim 2, further comprising:
    coating the upper surface of stage with the protection material before positioning the wafer slice.

4. The method of claim 3, wherein compressing the protection material comprises:
    providing a covering member adapted to fit over the top surface of the wafer slice and around the side surfaces of the wafer slice following the step of coating the wafer slice with the protection material.

5. The method of claim 4, wherein compressing the protection material further comprises:
    compressing the protection material to the wafer slice using the covering member.

6. The method of claim 5, further comprising:
    cooling the stage after compressing the protection material.

7. The method of claim 1, wherein the protection material comprises an epoxy resin compound.

8. The method of claim 4, wherein the covering member is formed in accordance with a shape of the wafer slice.

9. A method of forming a specimen for a transmission electron microscope (TEM) inspection, the method comprising:
    cutting a wafer slice from a wafer, the wafer slice comprising a beveled side surface comprising an inspection point;
    forming a protection layer on the wafer slice protecting the inspection point;
    forming a first preliminary specimen by cutting the wafer slice, wherein the first preliminary specimen comprises the inspection point;
    forming a second preliminary specimen by grinding top and bottom surfaces of the first preliminary specimen, wherein the second preliminary specimen comprises the inspection point; and,
    forming a specimen by etching portions of top and bottom surfaces of the second preliminary specimen around the inspection point to respective predetermined depths.

10. The method of claim 9 wherein forming the protective layer on the wafer slice comprises:
   coating the wafer slice with a protection material on top, bottom and side surfaces, wherein one of the side surfaces comprises the beveled side surface; and,
   compressing the protection material to the wafer slice.

11. The method of claim 10, further comprising:
   heating a stage adapted to support the wafer slice prior to coating with the protection material; and,
   positioning the wafer slice on an upper surface of the stage.

12. The method of claim 11, further comprising:
   coating the upper surface of stage with the protection material before positioning the wafer slice.

13. The method of claim 12, wherein compressing the protection material comprises:
   providing a covering member adapted to fit over the top surface of the wafer slice and around the side surfaces of the wafer slice following the step of coating the wafer slice with the protection material.

14. The method of claim 13, wherein compressing the protection material further comprises:
   compressing the protection material to the wafer slice using the covering member.

15. The method of claim 14, further comprising:
   cooling the stage after compressing the protection material.

16. The method of claim 9, wherein the protection material comprises an epoxy resin compound.

17. The method of claim 13, wherein the covering member is formed in accordance with a shape of the wafer slice.

18. The method of claim 9, wherein forming the second preliminary specimen comprises:
   securing the first preliminary specimen to a stage such that the inspection point faces in a direction parallel to the surface of the stage; and,
   grinding the first preliminary specimen.

19. The method of claim 9, wherein the second preliminary specimen is ground while the inspection point is viewed.

* * * * *